(12) United States Patent
Crespo Crespo et al.

(10) Patent No.: US 6,518,303 B2
(45) Date of Patent: Feb. 11, 2003

(54) 2-PHENYLPYRAN-4-ONE DERIVATIVES

(75) Inventors: Maria Isabel Crespo Crespo, Barcelona (ES); Juan Miguel Jimenez Mayorga, Barcelona (ES); Carles Puig Duran, Barcelona (ES); Lidia Soca Pueyo, Barcelona (ES)

(73) Assignee: Almirall Prodesfarma S.A., Barcelona (ES)

( * ) Notice: Subject to any disclaimer, the term of this patent is extended or adjusted under 35 U.S.C. 154(b) by 0 days.

(21) Appl. No.: 09/809,645

(22) Filed: Mar. 16, 2001

(65) Prior Publication Data

US 2002/0045644 A1 Apr. 18, 2002

Related U.S. Application Data

(63) Continuation of application No. PCT/EP99/06873, filed on Sep. 16, 1999.

(51) Int. Cl.⁷ ................... A61K 31/35; C07D 309/30; C07D 309/38
(52) U.S. Cl. ................... 514/459; 514/460; 549/292; 549/294; 549/293
(58) Field of Search ............... 549/62, 64, 65, 549/66, 292, 294, 293; 514/460, 459

(56) References Cited

U.S. PATENT DOCUMENTS

| | | | |
|---|---|---|---|
| 3,901,908 A | 8/1975 | Fitzi et al. | 260/309 |
| 304,728 A | * 12/1981 | Clark et al. | |
| 4,304,728 A | * 12/1981 | Clark et al. | 260/399 |
| 6,048,850 A | 4/2000 | Young et al. | 514/183 |

FOREIGN PATENT DOCUMENTS

| | | |
|---|---|---|
| EP | 0 714 883 A1 | 6/1996 |
| GB | 2 047 697 A | 12/1980 |
| WO | WO 95/14014 | 5/1995 |
| WO | WO 96/06840 | 3/1996 |
| WO | WO 96/31509 | 10/1996 |
| WO | WO 99/25697 | 5/1999 |

OTHER PUBLICATIONS

Saettone J. Org. Chem. 31, p. 1959 (1966) A Novel Route to 1,3,5–Trisubstituted Hydantoins.
Valenta et al Czech Chem. Comm. 48, 5, p. 1447–1464 (1983) XP–002127318.
Chemical Abstract XP 002127320 Protiva et al. 12/74 Parasympatholytic piperazine derivatives.

* cited by examiner

Primary Examiner—Alan L. Rotman
Assistant Examiner—Binta Robinson
(74) Attorney, Agent, or Firm—Nixon & Vanderhye

(57) ABSTRACT

2-Phenylpyran-4-one derivatives of formula (I):

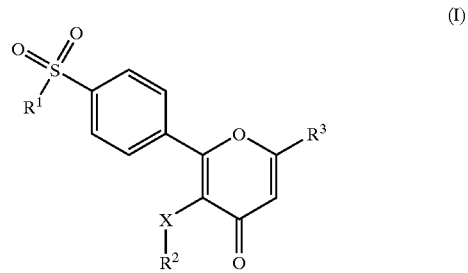

wherein:

$R^1$ represents an alkyl or —$NR^4R^5$ group, wherein $R^4$ and $R^5$ each independently represents a hydrogen atom or an alkyl group;

$R^2$ represents an alkyl, $C_3$–$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxalkyl or hydroxycarbonyl groups;

$R^3$ represents a methyl, hydroxymethyl, alkoxymethyl, $C_3$–$C_7$ cycloalkoxymethyl, benzyloxymethyl, hydroxycarbonyl, nitrile, trifluoromethyl or difluoromethyl group or a $CH_2$—$R^6$ group wherein $R^6$ represents an alkyl group; and X represents a single bond, an oxygen atom, a sulfur atom or a methylene group;

or pharmaceutically acceptable salts thereof, processes for their production and synthetic intermediates used in said processes, pharmaceutical compositions containing them and their use in medical treatment.

10 Claims, No Drawings

2-PHENYLPYRAN-4-ONE DERIVATIVES

This is a continuation of PCT application No. PCT/EP99/06873, filed Sep. 16, 1999, the entire content of which is hereby incorporated by reference in this application.

This invention relates to new therapeutically useful 2-phenylpyran-4-one derivatives, to processes for their preparation and to pharmaceutical compositions containing them.

It is known that nonselective inhibition of the enzyme cyclooxygenase (COX) prevents the overproduction of prostaglandins associated with inflammation, which are mediated by cyclooxygenase-2 (COX-2) bu., at the same time, deprives tissues of basal levels of prostaglandins necessary for the health of certain tissues mediated largely by cyclooxygenase-1 (COX-1). Non steroidal antiinflammatory drugs are non-selective inhibitors of COX and for that reason, have side effects of decreased renal blood flow, decreased platelet function, dyspepsia and gastric ulceration.

We have now found that certain 2-phenylpyran-4-one derivatives selectively inhibit COX-2 in preference to COX-1 and are useful in the treatment of COX-2 mediated diseases, such as inflammation, pain, fever and asthma with fewer side effects.

Accordingly the present invention provides a 2-phenylpyran-4-one compound of formula (I):

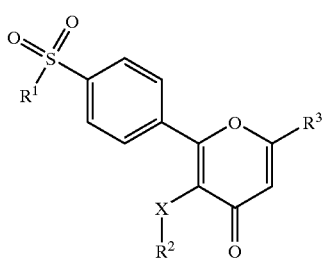

(I)

wherein $R^1$ represents an alkyl or —$NR^4R^5$ group, wherein $R^4$ and $R^5$ each independently represents a hydrogen atom or an alkyl group;

$R^2$ represents an alkyl, $C_3$–$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents a methyl, hydroxymethyl, alkoxymethyl, $C_3$–$C_7$ cycloalkoxymethyl, benzyloxymethyl, hydroxycarbonyl, nitrile, trifluoromethyl or difluoromethyl group or a $CH_2$—$R^6$ group wherein $R^6$ represents an alkyl group; and X represents a single bond, an oxygen atom, a sulfur atom or a methylene group;

or a pharmaceutically acceptable salt thereof.

The alkyl groups and moieties such as those present in the alkoxy, hydroxyalkyl, mono- or di-alkylamino groups, mentioned in relation to the groups $R^1$ to $R^6$ are usually "lower" alkyl that is containing from 1 to 6 particularly from 1 to 4 carbon atoms, the hydrocarbon chain being branched or straight. Preferred alkyl groups, and where relevant alkyl moieties, include methyl, ethyl, propyl including i-propyl, and butyl including n-butyl, t-butyl and sec-butyl.

In a phenyl group substituted by one or more halogen atoms or alkyl, trifluoroalkyl, hydroxy, alkoxy, methylthio, amino, mono- or dialkyl amino, hydroxyalkyl or hydroxycarbonyl groups, the phenyl ring may be substituted by 1, 2, 3, 4 or 5 substituents, preferably 1, 2 or 3 substituents, each being independently selected from the possible substituents set out above. The phenyl group (attached to X or the pyran-4-one ring through its 1-position) may be substituted at any of the remaining positions, that is to say the 2, 3, 4, 5 or 6-positions. A phenyl group having more than one substituent may be substituted at any combination of positions. For example a phenyl group having two substituents may be substituted at the 2 and 3, 2 and 4, 2 and 5, 2 and 6, 3 and 4 or 3 and 5 positions.

In particular, it is preferred that $R^2$ represents a branched alkyl, $C_3$–$C_7$ (preferably $C_3$, $C_5$ or $C_6$) cycloalkyl, napthyl, tetrahydronaphthyl or indanyl group, an unsubstituted phenyl group or a phenyl group substituted by one or more halogen atoms, alkoxy groups, preferably methoxy groups, and/or alkyl groups, preferably methyl groups. The phenyl group preferably has 1, 2 or 3 substituents, more preferably 1 or 2 substituents. Halogen atoms are preferably selected from fluorine, chlorine and bromine atoms. When $R^2$ as a phenyl group substituted by one or more halogen atoms, alkoxy groups and/or alkyl groups, preferably one of the substitutions is at the 4-position of the phenyl group. When $R^2$ is a phenyl group substituted by one or two halogen atoms at least one of the substitutions is preferably on the 2- or the 4-position.

It is preferred that $R^1$ independently represents an unsubstituted alkyl croup such as methyl, ethyl, propyl or butyl, preferably methyl, or an $NH_2$ group (i.e. $PR^4$ and $R^5$ in the above formula both independently represent an H atom)

It is also preferred that $R^3$ independently represents an unsubstituted alkyl group such as methyl, ethyl, propyl or butyl, preferably methyl, a nitrile group, a hydroxymethyl group, a methoxymethyl group, a difluoromethyl group or a hydroxycarbonyl group.

It is further preferred that X independently represents a single bond, an oxygen atom or a methylene group more preferably a single bond or an oxygen atom.

Specific examples of the 2-phenylpyran-4-one derivatives of the present intention include:
2-(4-methanesulfonylphenyl) -6-methyl-3-phenylpyran-4-one,
3-(4-fluorophenyl)-2-(4-methanesulfonylphenyl)-6-methylpyran-4-one,
3-(3-fluorophenyl)-2-(4-methanesulfonylphenyl)-6-methylpyran-4-one,
3-(2-fluorophenyl)-2-(4-methanesulfonylphenyl)-6-methylpyran-4-one,
3-(4-chlorophenyl)-2-(4-methanesulfonylphenyl)-6-methylpyran-4-one,
3-(3-chlorophenyl)-2-(4-methanesulfonylphenyl)-6-methylpyran-4-one,
3-(2-chlorophenyl)-2-(4-methanesulfonylphenyl)-6-methylpyran-4-one,
3-(4-bromophenyl)-2-(4-methanesulfonylphenyl)-6-methylpyran-4-one,
2-(4-methanesulfonylphenyl)-6-methyl-3-p-tolylpyran-4-one,
2-(4-methanesulfonylphenyl)-6-methyl-3-m-tolylpyran-4-one,
2-(4-methanesulfonylphenyl)-6-methyl-3-o-tolylpyran-4-one,
2-(4-methanesulfonylphenyl)-6-methyl-3-(4-trifluoromethylphenyl)pyran-4-one,
3-(2,4-difluorophenyl)-2-(4-methanesulfonylphenyl)-6-methylpyran-4-one, 3-(3,4-difluorophenyl)-2-(4-methanesulfonylphenyl)-6-methylpyran-4-one,
3-(3,5-difluorophenyl)-2-(4-methanesulfonylphenyl)-6-methylpyran-4-one,
3-(2,5-difluorophenyl)-2-(4-methanesulfonylphenyl)-6-methylpyran-4-one,
3-(2,6-difluorophenyl)-2-(4-methanesulfonylphenyl)-6-methylpyran-4-one,
3-(2,4-dichlorophenyl)-2-(4-methanesulfonylphenyl)-6-methylpyran-4-one,
3-(3,4-dichlorophenyl)-2-(4-methanesulfonylphenyl)-6-methylpyran-4-one,
3-(3-fluoro-4-methoxyplenyl)-2-(4-methanesulfonylphenyl)-6-methylpyran-4-one,
3-(4-chloro-3-fluorophenyl)-2-(4-methanesulfonylphenyl)-6-methylpyran-4-one,
3-(2-chloro-4-fluorophenyl)-2-(4-methanesulfonylphenyl)-6-methylpyran-4-one,
3-(4-bromophenoxy)-2-(4-methanesulfonylphenyl)-6-methylpyran-4-one,
3-(4-fluorophenoxy)-2-(4-methanesulfonylphenyl)-6-methylpyran-4-one
3-(2,4-difluorophenoxy)-2-(4-methanesulfonylphenyl)-6-methylpyran-4-one, 3-cyclohexyl-2-(4-methanesulfonylphenyl)-6-methylpyran-4-one,
2-(4-methanesulfonylyphenyl)-6-methyl-3-naphthalen-2-ylpyran-4-one,
4-(6-methyl-4-oxo-3-phenyl-4H-pyran-2-yl)benzenesulfonamide,
4-[3 (4-fluorophenyl)-6-methyl-4-oxo-4H-pyran-2-yl]benzenesulfonamide,
4-[3-(3,4-dichlorophenyl)-6-methyl-4-oxo-4H-pyran-2-yl]benzenesulfonamide,
5-(2,4-difluorophenyl)-6-(4-methanesulfonylphenyl)-4-oxo-4-pyran-2-carbontrile
3-(2-fluorophenoxy)-2-(methanesulfonylphenyl)-6-methylpyran-4-one,
3-(4-chlorophenoxy)-2-(methanesulfonylphenyl)-6-methylpyran-4-one,
3-(2-chlorophenoxy)-2-(methanesulfonylphenyl)-6-methylpyran-4-one,
3-(2,5-difluorophenoxy)-2-(methanesulfonylphenyl)-6-methylpyran-4-one,
3-(3-chloro-4-methylphenyl)-2-(4-methanesulfonylphenyl)-6-methylpyran-4-one,
2-(4-methanesulfonylphenyl)-6-methyl-3-phenoxypyran-4-one,
3-(4-fluorophenoxy)-2-(4-methanesulfonylphenyl)-6-methylpyran-4-one,
2-(4-methanesulfonylphenyl)-6-methyl-3-(4-methylphenoxy) pyran-4-one,
3-(4-chlorophenyl)-2-(4-methanesulfonylphenyl)-methoxymethylpyran-4-one,
3-(4-chlorophenyl)-6-difluoromethyl-2-(4-methanesulfonyl-phenyl) pyran-4-one,
and anyone of the compounds specifically identified in Table 4, and pharmaceutically acceptable salts thereof.
Of outstanding interest are:
3-(4-fluorophenyl)-2-(4-methanesulfonylphenyl)-6-methylpyran-4-one,
3-(2-fluorophenyl)-2-(4-methanesulfonylphenyl)-6-methylpyran-4-one,
3-(4-chlorophenyl)-2-(4-methanesulfonylphenyl)-6-methylpyran-4-one,
3-(4-bromophenyl)-2-(4-methanesulfonylphenyl)-6-methylpyran-4-one,
3-(2,4-difluorophenyl)-2-(4-methanesulfonylphenyl)-6-methylpyran-4-one,
3-(3,4-dichlorophenyl)-2-(4-methanesulfonylphenyl)-6-methylpyran-4-one,
3-(3-chloro-4-methylplenyl)-2-(4-methanesulfonylphenyl)-6-methylpyran-4-one,
2-(4-methanesulfonylphenyl)-6-methyl-3-phenoxypyran-4-one,
3-(4-fluorophenoxy)-2-(4-methanesulfonylphenyl)-6-methylpyran-4-one,
3-(2-fluorophenoxy)-2-(methanesulfonylphenyl)-6-methylpyran-4-one,
3-(4-chlorophenoxy)-2-(methanesulfonylphenyl)-6-methylpyran-4-one,
3-(2-chlorophenoxy)-2-(methanesulfonylphenyl)-6-methylpyran-4-one,
3-(4-bromophenoxy)-2-(4-methanesulfonylphenyl)-6-methylpyran-4-one,
2-(4-methanesulfonylphenyl)-6-methyl-3-(4-methylphenoxy) pyran-4-one,
3-2,4-difluorophenoxy)-2-(4-methanesulfonylphenyl)-6-methylpyran-4-one,
3-(2,5-difluorophenoxy)-2-(4-methanesulfonylphenyl)-6-methylpyran-4-one,
3-(4-chlorophenyl)-2-(4-methanesulfonylphenyl)-6-methoxymethylpyran-4-one,
3-(4-chlorophenyl)-6-difluoromethyl-2-(4-methanesulfonylphenyl)pyran-4-one,
and pharmaceutically acceptable salts thereof.

The present invention also provides processes for preparing a compound of formula (I) which depend on the definition of $R^3$. When $R^3$ is a methyl group, compounds of formula (I) are prepared according to the definition of $R^1$. Thus, compounds of formula (I) in which $R^3$ is a methyl group and $R^1$ is an alkyl or —$NR^4R^5$ group in which $R^4$ and $R^5$ are alkyl groups, viz. a 2-phenylpyran-4-one derivative of formula (II):

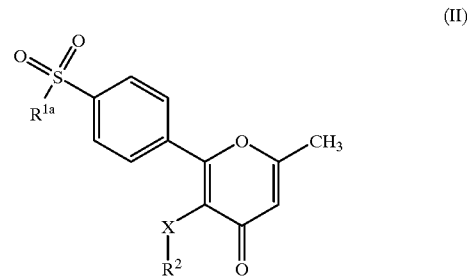

(II)

wherein $R^{1a}$ is an alkyl or —$NR^{4a}R^{5a}$ group in which $R^4a$ and $R^{5a}$ are each independently alkyl groups, and $R^2$ and X are as defined above, which comprises reacting a carbonyl derivative of formula (III):

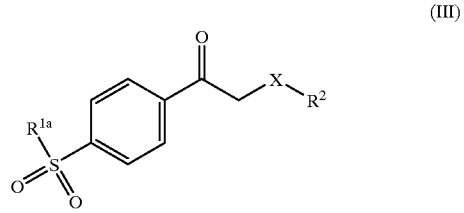

(III)

wherein $R^{1a}$, $R^2$ and X are as defined above with an excess of anhydrous acetic acid and polyphosphoric acid at a temperature from 100° C. to 150° C.

The carbonyl derivative of formula (III) may be obtained by methods well known in the literature (E-A-7148831

WO96/06840; WO96/31509an and DE-204520) or when X represents an oxygen or sulfur atom, by reacting a phenacyl derivative of formula (IV):

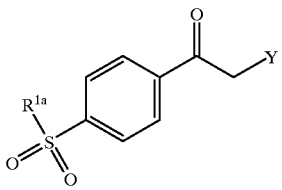

wherein $R^{1a}$ is as defined above and Y represents a chlorine or bromine atom, with a hydroxy or mercapto derivative of formula (V):

       (V)

wherein 2 is as defined above and $X^a$ is an oxygen or sulfur atom.

The reaction between the phenacyl derivative of formula (IV) and the intermediate compound of formula (V) may be carried out by heating a mixture of these two starting materials, optionally in a solvent mixture of methylene chloride, benzene or toluene and water, at a temperature of from 15° C. to 30° C. and in the presence of a phase transfer catalyst as benzyltriethylamonium chloride.

The carbonyl derivative of formula (III) in which X is other than a sulfur atom, may also be prepared by reacting a thio derivative of formula (VI):

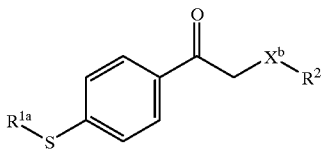

wherein $R^{1a}$ and $R^2$ are as defined above, and $X^b$ is a single bond, an oxygen atom or a methylene group, with an oxidizing agent, preferably magnesium monoperoxyphthalate or 3-chloroperoxybenzoic acid. The reaction is preferably carried out in an organic solvent such as a mixture of methylene chloride with methanol or ethanol, at a temperature of from 10° C. to 40° C.

The present invention also provides a process for the preparation of a compound of formula (I) wherein $R^3$ is a methyl group, $R^1$ is an alkyl group, and X is other than a sulfur atom viz. 2-phenylpyran-4-one derivative of formula (VII):

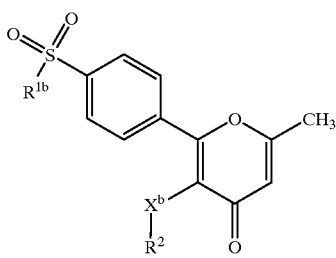

wherein $R^{1b}$ is an alkyl group and $R^2$ and $X^b$ are as defined above by reacting a mercapto derivative of formula (VIII):

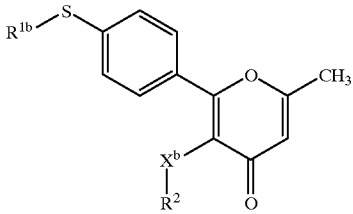

wherein $R^{1b}$, $R^2$ and $X^b$ are as defined above with an oxidizing agent, preferably with magnesium monoperoxyphthalate or 3-chloroperoxybenzoic acid The reaction between the mercapto derivative of formula (VIII) and the oxidizing agent is preferably carried out, as previously disclosed for the compound of formula (VI), in an organic solvent such as a mixture of methylene chloride with methanol or ethanol, at a temperature of from 10° C. to 40° C.

The present invention additionally provides a process for the preparation of a compound of formula (I) wherein $R^1$ is a —$NR^4R^5$ group and $R^3$ is a methyl group, viz. 2-phenylpyran-4-one derivative of formula (IX):

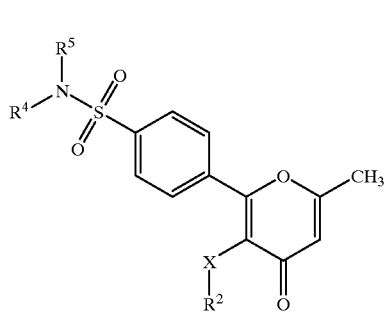

wherein $R^2$, $R^4$, $R^5$ and X are as defined above by reacting a chlorosulfonyl derivative of formula (X):

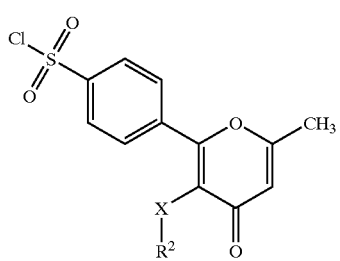

wherein $R^2$ and X are as defined above with an amine of formula (XI):

       (XI)

wherein $R^4$ and $R^5$ are as defined above.

This reaction is preferably carried out at a temperature Of from 10° C. to 40° C.

The chlorosulfonyl derivative of formula (X) may, for example, be prepared by reacting a compound of formula (XII):

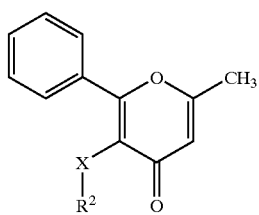

(XII)

wherein R² and X are as defined above with chlorosulfonic acid, preferably at a temperature of from 80° C. to 120° C.

The present invention further provides a process for the preparation of a compound of formula (I) wherein R³ is a methyl group and R¹ is a group wherein R⁴ and R⁵ are hydrogen, viz, the 2-phenylpyran-4-one derivative of formula (XIII):

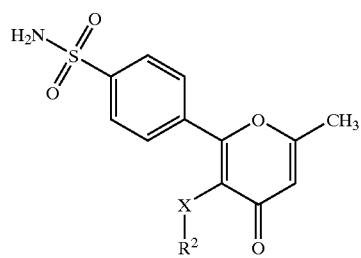

(XIII)

wherein R² and X are as defined above by debenzylation of the corresponding N,N-dibenzyl derivative of formula (XIV):

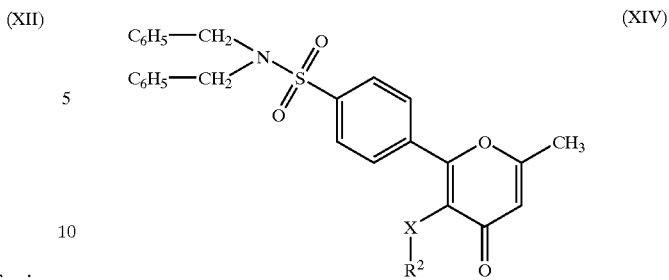

(XIV)

wherein R² and X are as defined above.

The debenzylation is preferably carried out with an excess of trifluoroacetic, sulfuric or methanesulfonic acid at a temperature of from 0° C. to 120° C.

The intermediate of formula (XIV) may be prepared according to the above processes using appropriate starting materials wherein R⁴ and R⁵ (or R⁴ᵃ and R⁵ᵃ) both represent benzyl groups.

The intermediate of formula (IV) and (VI) used in the preparation of the compounds of the invention may be prepared by methods disclosed in the literature, for example, in M. F. Saettone, J. Org. Chem. 31, p 1959 (1966) and WO-9606840.

The intermediate compounds of formulae (VIII) and (XII) may be prepared by the same process disclosed for the preparation of compounds of formula (II), with the appropriate starting materials.

The 2-phenylpyran-4-one derivatives of formula (I) wherein R³ is other than a methyl group, can be prepared by processes which are represented in the following scheme:

Scheme

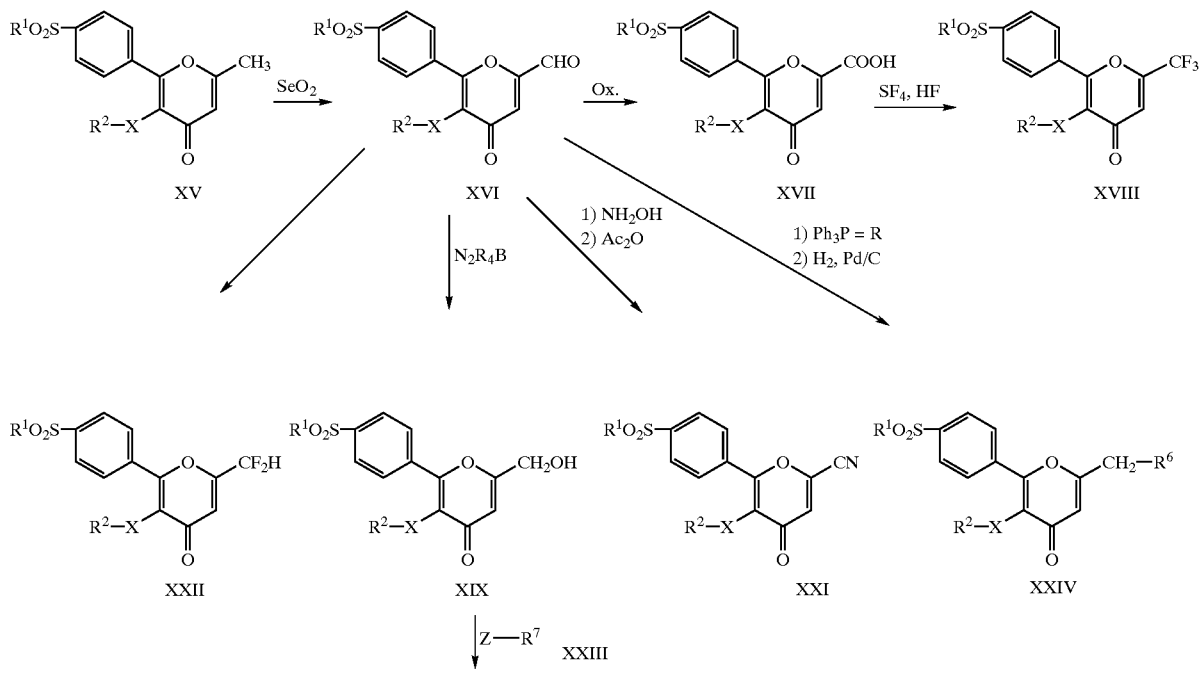

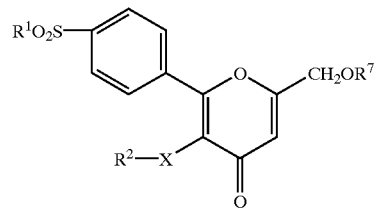

As can be seen in the scheme, 2-phenylpyran-4-one derivatives of formula (I) wherein $R^3$ is other than a methyl group, viz. compounds of formulae (XVII), (XVIII), (XIX), (XX), (XXI), (XXII) and (XXIV), are prepared from compounds of formula (I) in which $R^3$ is a methyl group, viz. compound of formula (XV), which processes of preparation have been disclosed above. In a first stage, compounds of formula (XV) are treated with an oxidizing agent as selenium dioxide in an organic solvent as tetrahydrofuran or dioxan, in a pressure vessel and at a temperature from 100° C. to 190° C. The corresponding aldehyde of formula (XVI) is obtained, which is used as starting material to obtain the compounds of formula (I) with $R^3$ other than a methyl group.

The compounds of Formula (I) wherein $R^3$ is a hydroxycarbonyl group, viz. compound of formula (XVII), are prepared from the corresponding aldehyde (XVI) by reaction with an oxidizing agent as pyridinium dichromate or manganese dioxide in an organic solvent as N,N-dimethylformamide or ethanol at a temperature between −5° C. and 35° C. The obtained compounds (XVII) are used as starting materials to obtain compounds of Formula (I) wherein $R^2$ is a trifluoromethyl group, viz. compound of formula (XVIII). The reaction is carried out by reaction of compounds (XVII) with a mixture of sulphur tetrafluoride and hydrogen fluoride, optionally in the presence of an organic solvent as methylene chloride, in a pressure vessel, and at a temperature from 20° C. to 140° C.

The compounds of formula (I) wherein $R^3$ represents a hydroxymethyl group viz. compounds of formula (XIX) are prepared by reduction of compounds (XVI) with a boron or aluminium hydride, preferably sodium borohydride in a solvent as methanol or ethanol and at a temperature from 10° C. to 40° C. Further reaction of compounds (XIX) with an appropriate halide of formula (XXIII):

Z—R⁷ (XXIII)

wherein Z represents a chlorine, bromine or iodine atom and $R^7$ represents an alkyl, $C_3$–$C_7$ cycloalkyl or benzyl group, provide the compounds of formula (I) wherein $R^3$ is an alkoxymethyl, $C_3$–$C_7$ cycloalkoxymethyl or benzyloxymethyl group viz. compounds of formula (XX). The reaction is carried out in an organic solvent such as acetone, N,N-dimethylformamide or tetrahydrofuran in the presence of sodium or potassium hydride or amide, and at a temperature between 20° C. and 120° C.

Also aldehydes of formula (XVI) are used as starting material to obtain compounds of formula (I) wherein $R^3$ is a nitrile group, viz. compounds of formula (XX:). The reaction is carried out n a first stage by treatment of aldehydes (XVI) with hydroxylamine hydrochloride and formic acid at a temperature from 80° C. to 120° C. The resulting oxime derivative is isolated and heated with an excess of acetic anhydride at a temperature between 100° C. to 180° C.

The compounds of formula (I) wherein $R^3$ represents a difluoromethyl group, viz. compounds of formula (XXII), are prepared from aldehydes of formula (XVI) by reaction with a fluorinated reagent as diethylaminosulfur trifluoride, or a mixture of sulfur tetrafluoride-hydrogen fluoride, optionally in the presence of an organic solvent as methylene chloride, benzene or toluene and at a temperature from 0° C. to 130° C.

The 2-phenylpyran-4-one derivatives of formula (I) in which $R^3$ is a $CH_2$—$R^6$ croup, viz. compounds of formula (XXIV), are also prepared from aldehydes of formula (XVI) in a two stages process. In the first stage, the aldehyde (XVI) is reacted with a triphenylphosphine derivative (XXV) in the presence of a solvent as dioxane, dimethoxyethane or tetrahydrofuran at a temperature from 15° C. to the boiling point of the solvent. The resulting compound is hydrogenated in the second stage of the process in the presence of a catalyst as palladium or activated carbon. The reaction is carried out in the presence of a solvent as methanol, ethanol or ethyl acetate at a temperature from 15° C. to 40° C.

The 2-phenylpyran-4-one derivatives of formula (I) in which there is the presence of a basic group, can be converted by methods know per se into pharmaceutically acceptable salts, preferably acid addition salts by treatment with organic or inorganic acids as fumaric, tartaric, succinic or hydrochloric acid. Also, 2-phenylpyran-4-one derivatives of formula (I) in which $R^3$ represents an hydroxycarbonyl group, may be converted into pharmacologically acceptable salts with, for instance, alkali metals such as sodium or potassium by reaction with an alkali metal hydroxide.

The following biological tests and data further illustrate this invention.

COX-1 and COX-2 activities in human whole blood

Fresh blood from healthy volunteers who had not taken any non-steroidal ante-inflammatory drugs for at least 7 days prior to blood extraction was collected in heparinized tubes (20 units of heparin per ml). For the COX-1 activity determination, 500 µl aliquots of blood were incubated with either 5 µl vehicle (dimethylsulphoxide) or 5 µl of a test compound for 1 h at 37° C. Calcium ionophore A23187 (25 µM) was added 20 min before stopping the incubation. Plasma was separated by centrifugation (10 min at 13000 rpm) and kept at −30° C. until $TXB_2$ levels were measured using an enzyme immunoassay kit (ELISA). The effect of the compounds were evaluated by incubating each compound at five to six different concentrations with triplicate determinations. $IC_{50}$ values were obtained by non-linear regression using InPlot, GraphPad software on an IBM computer.

For the COX-2 activity determination, 500 µl aliquots of blood were incubated in the presence of LPS (10 µg/ml) for 24 h at 37° C. in order to induce The COX-2 expression (Patriagnani et al., J. Pharm. Exper. Ther. 271; 1705–1712 (1994)). Plasma was separated by centrifugation (10 min at 13000 rpm.) and kept at −30° C. until $PGE_2$ levels were measured using an enzyme immunoassay kit (ELISA). The effects of inhibitors were studied by incubating each compound (5 µl aliquots) at five to six different concentrations with triplicate determinations in the presence of LPS for 24 hours. $IC_{50}$ values were obtained by non-linear regression using InPlot, GraphPad software on an IBM computer.

Anti-inflammatory activity (adjuvant arthritis)

Male Wistar rats weighing 175–200 g with free access to food and water were used. On day 0, the animals received an intraplantar injection of a suspension of Mycobacterium tuberculosis in paraffin oil (0.5 mg/rat) on the left hind paw. A group of nonarthritic control rats were injected with paraffin oil alone. On days 11 and 14 after induction of arthritis, the volume of the hind paw of each rat was measured using a water plethysmograph. Animals whose paw volumes increased during that time were selected. Rats were distributed into groups of 8 having equal mean paw volumes and an approximately equal standard deviation Test compounds were administered p.o. once daily for 7 days (days 14–20). Nonarthritic and arthritic control rats received vehicle alone for 7 days. The hind paw volumes were measured 20 h after the last dose (on day 21). The body weight was determined every second day.

The results were expressed as the percentage of inhibition of inflammation (paw volume) for each treatment group, considering both the arthritic and nonarthritic vehicle controls. The ANOVA tests was used for statistical studies.

Ulcerogenic activity

Animals: Male Wistar rate (Interfauna, U.K., Ltd.) weighing about 150–175 g were used. Animals were maintained on a 12:12 hour light-dark cycle (lights on at 7:00 am) at room temperature (22±1° C.). Food and water were allowed ad libitum.

Procedure: The compounds were administered by the oral route once a day for 4 consecutive days. The body weight of each rat was assessed every day before drug administration. The animals were anesthesized 24 h after the last dosing and 1 ml of blood was extracted by cardiac puncture using heparin (10 U/ml) as anticoagulant. The percentage of hematocrit was measured. The intestines were removed, opened longitudinally and gently washed. The macroscopic severity of the intestinal erosions was assessed using a parametric scale, evaluating the number of the perforated and non-perforated intestinal ulcers by means of a lesion index ranging from 0 to 3 (0:no ulcers, 1:<10 ulcers, 2:10–25 ulcers to 3:>25 ulcers). No gastric ulcers are observed using this protocol.

The treatments were randomized in each experiment. The results were compared with those obtained in the vehicle-treated group using the ANOVA test.

Results

The results obtained from the biological assays are shown in Table 1, 2 and 3.

TABLE 1

COX-1 and COX-2 Inhibition

| Compound (*) | COX-1 $IC_{50}$ (μM) | COX-2 $IC_{50}$ (μM) | Ratio COX-1/COX-2 |
|---|---|---|---|
| Indomethacin | 0.19 | 0.22 | 0.86 |
| 2 | >100 | 1.06 | >94 |
| 4 | >100 | 1.5 | >66 |
| 5 | >100 | 2.1 | >47 |
| 8 | >100 | 1.7 | >58 |
| 15 | 100 | 1.1 | 90 |
| 22 | 37.1 | 0.7 | 53 |
| 31 | >100 | 1.67 | >59 |
| 37 | >100 | 1.08 | >92 |
| 39 | >100 | 0.96 | >104 |
| 40 | 27 | 0.14 | 193 |

TABLE 1-continued

COX-1 and COX-2 Inhibition

| Compound (*) | COX-1 $IC_{50}$ (μM) | COX-2 $IC_{50}$ (μM) | Ratio COX-1/COX-2 |
|---|---|---|---|
| 41 | >100 | 0.35 | >285 |
| 42 | 41 | 0.2 | 205 |
| 43 | >100 | 0.8 | 125 |
| 44 | 39 | 0.21 | 185 |
| 45 | 22 | 0.15 | 147 |
| 47 | 57.1 | 0.8 | 71 |
| 63 | 44 | 1.73 | 25 |
| 67 | >100 | 2.1 | >47 |

(*) See structures in Table 4.
Indomethacin is 1-(4-chlorobenzoyl)-5-methoxy-2-methylindole-3-acetic acid.

TABLE 2

Anti-inflammatory activity

| Compound | % Inhibition (dose, mg/kg) |
|---|---|
| Indomethacin | 64 (1) |
| 5 | 50 (1) |
| 22 | 69 (1) |
| 39 | 75 (1) |
| 41 | 71 (1) |
| 45 | 74 (1) |

TABLE 3

Ulcerogenic activity

| Compound | Dose (mg/kg) | Lesion index PU | Lesion index NPU | Hematocrit (%) |
|---|---|---|---|---|
| Vehicle | | 0 | 0 | 44.3 ± 0.2 |
| Tridomethacin | 10 | 3 | 3 | 22.7 ± 1.6 |
| 5 | 100 | 0 | 0 | 44.1 ± 0.7 |
| 22 | 100 | 0 | 0 | 44.4 ± 0.3 |
| 39 | 100 | 0 | 0 | 43.7 ± 0.4 |
| 41 | 100 | 0 | 0 | 43.4 ± 1.9 |
| 45 | 100 | 0 | 0 | 44.4 ± 0.9 |

PU: perforated ulcers,
NPU: non-perforated ulcers.

As shown in Table 1, the 2-phenylpyran-4-ore derivatives of formula (I) are potent and selective COX-2 inhibitors whereas the reference compound indomethacin is as equipotent as COX-2 and COX-1 inhibitor. Due to their low COX-1 inhibitory activity, the compounds of formula (I) present an important anti-inflammatory activity (see Table 2) and the benefit of significantly less harmful side effects than the non-steroidal anti-inflammatory drugs commonly used (e.g. gastrointestinal toxicity (see Table 3), renal side-effects, reduced effect on bleeding times and asthma induction in aspirin-sensitive subjects).

Thus the compounds of the invention are preferably selective inhibitors of mammalian COX-2, for example human COX-2. The compounds of the invention also preferably have low inhibitory activity toward mammalian COX-1, for example human COX-1. Inhibitory activity can typically be measured by in vitro assays, or example as described above.

Preferred compounds of the invention have an $IC_{50}$ value for COX-2 of less than 5 μm, preferably less than 3 more preferably less than 2.5 μm. Preferred compounds of the invention also have an $IC_{50}$ value for COX-1 of greater than 10 µM, preferably greater than 20 µM. As an indicator of selectivity for inhibition of COX-2 over COX-1, the ratio of COX-1/COX-2 $IC_{50}$ values is preferably greater than 20, 30 or 50, more preferably greater than 80, 90 or 100.

The present invention further provides a compound of formula (I) for use in a method of treatment of the human or animal body by therapy, in particular for the treatment of pain, fever or inflammation, to inhibit prostanoid-induced smooth muscle contraction or for the prevention of colorectal cancer or neurodegenerative diseases.

The present invention further provides the use of a compound of formula (I) in the manufacture of a medicament for the treatment of pain,, fever or inflammation, to inhibit prostanoid-induced smooth muscle contraction or for the prevention of colorectal cancer or neurodegenerative diseases.

The compounds of formula (I) are useful for relief of pain, fever and inflammation of a variety of conditions including rheumatic fever, symptoms associated with influenza or other viral infections, common cold, low back and neck pain, dysmenorrhoea, headache, toothache, sprains and strains, myositis, neuralgia, synovitis, bursitis, tendinitis, injuries, following surgical and dental procedures and arthritis including rheumatoid arthritis, osteoarthritis, gouty arthritis, spondyloarthopathies, systemic lupus erythematosus and juvenile arthritis and bone resorption. They may also be used in the treatment of skin inflammation disorders such as psoriasis, eczema, burning and dermatitis. In addition, such compounds may be used for the prevention of colorectal cancer.

The compounds of formula (I) well also inhibit prostanoid-induced smooth muscle contraction and therefore may be used in the treatment of dysmenorrhoea, premature labour, asthma and bronchitis.

The compounds of formula (I) can be used as alternative to conventional non-steroidal anti-inflammatory drugs, particularly where such non-steroidal anti-inflammatory drugs way be contraindicated such as the treatment of patients with gastrointestinal disorders including peptic ulcers, gastritis, regional enteritis, ulcerative colitis, diverticulitis, Crohn's disease, inflammatory bowel syndrome and irritable bowl syndrome, gastrointestinal bleeding and coagulation disorders, kidney disease (e.g. impaired renal function), those prior to surgery or taking anticoagulants, and those susceptible to non-steroidal anti-inflammatory drugs induced asthma.

The compounds can further be used to treat inflammation in diseases such as vascular diseases, migraine headaches, periarteritis nodosa, thyroiditis, aplastic anaemia, Hodgkin's disease, scleroderma, type I diabetes, myasthenia gravis, sarcoidosis, nephrotic syndrome, Behcet's syndrome, polymyositis, hypersensitivity, conjunctivitis, gingivitis, myocardial ischaemia and stroke.

Compounds of the present invention are inhibitors of cyclooxygenase-2 enzyme and are thereby useful to treat the cyclooxygenase-2 mediated diseases enumerated above. These compounds can further be used for the prevent on of neurodegenerative diseases such as Alzheimer's disease.

Accordingly, the 2-phenylpyran-4-one derivatives of formula (I) and pharmaceutically acceptable salts thereof, and pharmaceutical compositions comprising such compounds and/or salts thereof, may be used in a method of treatment of disorders of the human body which comprises administering to a patient requiring such treatment an effective amount of a 2-phenylpyran-4-one derivative of formula (I) or a pharmaceutically acceptable salt thereof.

The present invention also provides pharmaceutical compositions which comprise, as an active ingredient, as least a 2-phenylpyran-4-one derivative of formula (I) or a pharmacologically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

Preferably the compositions are made up in a form suitable for oral, topical, nasal, inhalation, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions so this invention are preferably adapted for injectable and per os administration. In this case, the compositions for oral administration may take the form of tablets, retard tablets, sublingual tablets, capsules or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a, pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 10–600 mg of active ingredient per day. Daily dosage may be administered in one or more treatments, preferably from 1 to 4 treatments, per day.

The invention is illustrated by the following Examples, which do not limit the scope of the invention in any way.

EXAMPLE 1 a) To a solution of 2-(4-fluorophenyl)-1-(4-methanesulfonylphenyl)ethanone (1 g; 3.4 moles) in glacial acetic acid (15 ml), polyphosphoric acid (10 g) was added and then heated at 140° C. for 16 hours. After cooling, the reaction was poured into ice-water, extracted with ethyl acetate (2×50 ml), the organic solution dried ($Na_2SO_4$) and the solvent removed under reduced pressure. The residual oil was purified by column chromatography with silica gel and ethyl acetate as eluent. 3-(4-fluorophenyl)-2-(4-methanesulfonylphenyl)-6-methylpyran-4-one was obtained (0.5 g) m.p. 237° C. (Compound 2 in Table 4).

EXAMPLE 2 a) To a solution of 2,4-difluorophenyl (3.71 g; 29 mmol) and 2-bromo-1-(4-methylsulfonylphenyl)ethanone (7.00 g;

29 mmol) in methylene chloride. (50 ml) was added a solution of potassium carbonate (5.91 g; 43 mmol) and tetrabutylammonium hydrogensulfate (0.48 g; 1.4 mmol) in water (20 ml) The mixture was stirred at room temperature for 16 hours. Water (100 ml) was added, the organic phase was decanted, and the basic phase was extracted with methylene chloride (2×100 ml) The organic solution was dried ($Na_2SO_4$) and the solvent removed under reduced pressure. The resulting solid was washed with ethyl ether. 2-(2,4-Difluorophenoxy)-1-(4-methylsulfanylphenyl) ethanone was obtained (6.60 g), m.p. 70–71° C.

b) To a solution of 2-(2,4-difluorophenoxy)-1-(4-methylsulfonyl)ethanone (6.60 g; 22 mmol) in methylene chloride (100 ml), water (20 ml) and 80% magnesium monoperoxyphatlate hexahydrate (15.26 g; 25 mmol) were added. The mixture was stirred at room temperature for 16 hours. The reaction was poured into saturated solution of sodium bicarbonate (200 ml) and extracted with methylene chloride (3×100 ml). The organic phase was dried ($Na_2SO_4$) and the solvent removed under reduced pressure. 2-(2 4-Difluorophenoxy)-1-(4-methanesulfonylphenyl)ethanone was obtained (4.97 g) as a solid, m.p. 161–163° C.

c) To a solution of 2-(2,4-Difluorophenoxy)-1-(4-methanesulfonylphenyl)ethanone ( 4.60 g; 14 mmol) in acetic acid (70 ml), polyphosphoric acid (45 g) was added and then heated at 140° C. for 5 hours. After cooling, the reaction was poured into ice-water, extracted with ethyl acetate (2×100 ml), the organic solution dried ($Na_2SO_4$) and the solvent removed under reduced pressure. The residual oil was purified by column chromatography with silica gel and ethyl acetate/n-hexane (1:2) as eluent. Recrystallization from ethanol gave 3-(2,4-difluorophenoxy)-2-(4-methanesulfonylphenyl)-6-methylpyran-4-one (0.64 g), m.p. 191° C. (Compound 45 in Table 4).

EXAMPLE 3 a) A solution of 4-(dibenzylsulfamoyl)benzoic acid (24 g; 63 mmoles) in thionyl chloride (50 ml) was boiled under reflux for 2.5 hours and the excess of thionyl chloride removed under reduced pressure. 4-(dibenzylsulfamoyl) benzoyl chloride (25 g) was obtained as an oil which was used in the next step without purification.

b) To a solution of N,O-dimethylhydroxylamine hydrochloride (7.37 g; 75.6 mmoles) and triethylamine (21.8 ml; 151 mmoles) in methylene chloride (150 ml), another solution of 4-(dibenzylsulfamoyl)benzoyl chloride (25 g) in methylene chloride (150 ml) was slowly added and the resulting mixture stirred at room temperature for 16 hours. The solid was filtered off, the solvent removed under reduced pressure and the residual oil purified by column chromatography with silica gel and n-hexane-ethyl acetate 1:1 as eluent. N,O-dimethylamide of 4-(dibenzylsulfamoyl) benzoic acid (22 g) was obtained, m.p. 75° C.

c) To a suspension of magnesium (2 g; 82.4 mmoles) in anhydrous tetrahydrofuran (20 ml), another solution of benzyl chloride (10.4 g; 82.4 mmoles) in anhydrous tetrahydrofuran (100 ml) was slowly added. When the reaction was completed, a solution of N,O-dimethylamide of 4-(dibenzylsulfamoyl)benzoic acid (7 g, 16.5 mmoles) in anhydrous tetrahydrofuran (50 ml) was slowly added while the temperature was maintained at 0° C. After stirring at the same temperature for half an hour, the reaction mixture was poured into an ammonium chloride saturated solution (100 ml), extracted with ethyl ether (3×75 ml) and the organic extracts dried ($Na_2SO_4$). The solvent was removed under reduced pressure an the residual oil was purified by column chromatography with silica gel and n-hexane-ethyl acetate 1:3 as eluent. N,N-dibenzyl-4-phenylacetylbenzesulfonamide (9.4 g) was obtained, m.p 143° C.

d) To a solution of the above compound obtained in c) (9.4 g; 20.7 mmoles) in glacial acetic acid (140 ml), polyphosphoric acid (94 g) was added and the resulting mixture heated to 140° C. for 16 hours. After cooling, the reaction mixture was poured into ice-water, extracted with ethyl acetate (3×150 ml) and the organic solution dried ($Na_2SO_4$). The solvent was removed in vacuo and to the residual oil, concentrated sulfuric acid (38 ml) was added, then stirred at 0° C. for 10 minutes, further 60 minutes at room temperature and poured into ice-water. The precipitated solid was collected by filtration and purified by column chromatography with silica gel and ethyl acetate as eluent. 4-(6-methyl-4-oxo-3-phenyl-4H-pyran-2-yl)benzenesulfonamide (1.5 g) was obtained, m.p. 218° C. (Compound 54 in Table 4)

EXAMPLE 4 a) To a solution of 3,4-dichlorophenylacetophenone (5.3 g; 20 mmoles) in glacial acetic acid (90 ml), polyphosphoric acid (64 g) was added and the resulting solution heated at 140° C. or 24 hours. After cooling, the reaction mixture was poured into ice-water, extracted with ethyl acetate (3×75 ml), the organic solution dried ($Na_2SO_4$) and the solvent removed under reduced pressure. The obtained residue was purified by column chromatography with silica gel and n-hexane-ethyl acetate 3:2 as eluent. 3-(3,4-dichlorophenyl)-2-phenyl-6-methylpyran-4-one (1.68 g) was obtained, m.p. 104° C.

b) A solution of the compound obtained above (1.4 g; 4.3 mmoles) in chlorosulfonic acid (12 ml) was heated at 70° C. for 1.5 hours and after cooling, the reaction mixture was slowly poured into ice-water and extracted with ethyl acetate (2×50 ml). The organic solution was dried ($Na_2SO_4$), the solvent removed under reduced pressure and to the residual oil, previously solved in methanol (10 ml), a saturated solution of ammoniac in methanol (40 ml) was slowly added. After stirring at room temperature for 1 hour, the solvent was removed under reduced pressure, the residue solved in ethyl acetate (100 ml) and the resulting solution was washed with water (2×100 ml), dried ($Na_2SO_4$) and the solvent removed under reduced pressure. The residual oil was purified by column chromatography wish silica gel and n-hexane-ethyl acetate 1:1 as eluent. 4-[3-(3,4-dichlorophenyl)-6-methyl-4-oxo-4H-pyran-2-yl] benzenesulfonamide (0.5 g) was obtained, m.p. 128° C. (Compound 56 in Table 4).

EXAMPLE 5 a) To a solution of N,N-dibenzyl-4-(2-bromoacetyl) benzenesulfonamide (10.5 g, 23 mmoles), and p-chlorophenol (2.94 g, 23 mmoles) in methylene chloride (42 ml), potassium carbonate (4.83 g, 34.7 mmoles) and tetrabutylammonium bromide (0.42 g, 1.2 mmoles) in water (140 ml)was added. The reaction mixture was refluxed for 16 hours. After cooling, the mixture was diluted with methylene chloride (150 ml). The organic layer was separated, washed with water, and dried ($Na_2SO_4$) The solvent was removed under reduced pressure. N,N-dibenzyl-4-[2-(4-chlorophenoxy)acetyl]benzenesulfonamide (11.7 g) was obtained as a semisolid residue, which was used in the next step without further purification.

b) To a solution of N,N-dibenzyl-4-[2-(4-chlorophenoxy) acetyl]benzenesulfonamide (11.7 g, 23 mmoles) in acetic acid(105 ml), polyphosphoric acid (75 g) was added and the resulting solution was heated at 140° C. for 5 hours. After cooling, the reaction mixture was poured into ice-water, extracted with ethyl acetate (3×150 ml), and the organic solution was dried ($Na_2SO_4$). The solvent was removed under reduced pressure and the resulting oil was solved in $H_2SO_4$ (33 ml). The mixture was stirred at room temperature for 15 minutes, and poured into ice-water. The solid was filtered off and purified by column chromatography silica gel and ethyl acetate/methylene chloride/acetic acid (78:10:1) as eluent. 4-[3-(4-chlorophenoxy)-6-methyl-4-oxo-4H-pyran-2-yl]benzenesulfonamide (0.28 g) was obtained. m.p. 221° C. (Compound 57 in Table 4).

EXAMPLE 6 a) To a solution of 3-(2,4-difluorophenyl)-2-(4-methanesulfonylphenyl)-6-methylpyran-4-one (1.7 g; 4.5 mmoles) (compound 13) in dioxane (45 ml), selenium dioxide (2.2 g, 20 mmoles) was added and the mixture heated in a pressure vessel at 180° C. for 1 hour. After cooling, the reaction mixture was filtered, the solvent removed under reduced pressure and the residual oil purified by column chromatography with silica gel and ethyl acetate as eluent. 5-(2,4difluorophenyl)-6-(4-methanesulfonylphenyl)-4-oxo-4H-pyran-2-carbaldehyde (0.85 g) was obtained.

b) To a solution of the above compound (0.8 g; 2.1 mmoles) in formic acid (6 ml), hydroxylamine hydrochloride (0.17 g; 2.7 mmoles) was added and the mixture heated at 100° C. for 2 hours. After cooling, the reaction mixture was poured into ice, 2N sodium hydroxide was added until pH=7 and extracted with ethyl acetate (2×50 ml. The organic solution was dried ($Na_2SO_4$) the solvent removed in vacuo and the residue was dissolved in acetic anhydride (15 ml) and heated at 150° C. for 3 hours. The solvent was removed under reduced pressure, the residue treated with methylene chloride (50 ml) and the resulting solution washed with 2N sodium hydroxide (2×25 ml). The organic solution was dried ($Na_2SO_4$), the solvent removed in vacuo and the residue purified by column chromatography with silica gel and n-hexane-ethyl acetate 1:1 as eluent. 5-(2,4-difluorophenyl)-6-(4-methanesulfonylphenyl)-4-oxo-4H-pyran-2-carbonitrile (0.2 g), m.p. 113° C. (Compound 59 in Table 4).

EXAMPLE 7 a) To a solution of 3-(4-chlorophenyl)-2-(4-methanesulfonylphenyl)-6-methylpyran-4-one (4.0 g, 10.6 mmoles) in dioxane (50 ml), selenium dioxide (5.9 g, 53 mmoles) was added and heated into a sealed tube at 180° C. for 30 minutes. After cooling, the raw material was filtered through Celite and the solvent was removed under reduced pressure. The resulting oil was purified by column chromatography with silica gel and ethyl acetate/n-hexane (2:1) as eluent. 5-(4-chlorophenyl)-6-(4-methanesulfonylphenyl)-4-oxo-4-pyran-2-carbaldehyde (1.80 g) was obtained.

b) To a solution of 5-(4-chlorophenyl)-6-(4-methanesulfonylphenyl)-4-oxo-4H-pyran-2-carbaldehyde (1.8 g, 4.6 mmoles) in methanol (30 ml), sodium borohydride (0.26 g, 6.9 mmoles)was slowly added at 0° C. The resulting mixture was stirred for 30 minutes at room temperature. The reaction mixture was concentrated and the residue was solved in ethyl acetate. The organic layer was washed with water, dried ($Na_2SO_4$), and the solvent was removed under reduced pressure. The resulting residue was purified by column chromatography with silica gel and ethyl acetate/n-hexane (1:1) as eluent. 3-4-chlorophenyl)-6-hydroxymethyl-2-(4-methanesulfonylphenyl)pyran-4-one (0.9 g) was obtained. m.p. 120° C. (Compound 60 in Table 4).

EXAMPLE 8 a) To a solution of 3-(4-chlorophenyl)-6-hydroxymethyl-2-(4-methanesulfonylphenyl)pyran-4-one (0.5 g, 1.3 mmoles) in methylene chloride (10 ml), methyl iodide (0.24 ml, 3.86 mmoles), and a solution of sodium hydroxide (0.41 g, 10.3 mmoles) and tetrabutylammonium chloride (50 ml) in water (0.8 ml) were added. The reaction mixture was stirred at room temperature for 18 hours. The organic layer was diluted with methylene chloride (20 ml), washed with water and dried ($Na_2SO_4$). The solvent was removed under reduced pressure. The resulting solid was purified by column chromatography with silica gel and ethyl acetate as eluent. 3-(4-chlorophenyl)-2-(4-methanesulfonylyphenyl)-6-methoxyphenylpyran-4-one (0.15 g) was obtained. m.p. 162° C. (Compound 63 in Table 4)

EXAMPLE 9 a) To a solution of silver nitrate (0.88 g, 5.1 mmoles) in water (4 ml), a solution of sodium hydroxide (0.42 g, 6.2 mmoles) in water (4 ml) was added. The reaction mixture was stirred for 15 minutes at room temperature, and a solution 5-(4-chlorophenyl)-6-(4-methanesulfonylphenyl)-4-one-4H-pyran-2-carbaldehyde in tetrahydrofuran (10 ml) was added. The reaction mixture was stirred for 3 hours at room temperature and filtered through Celite. The solvent was removed under reduced pressure and the residue was solved in ethyl acetate. The organic layer was washed with water and dried ($Na_2SO_4$). The solvent was removed under reduced pressure. The resulting solid was purified by column chromatography with silica gel and ethyl acetate/methylene chloride/acetic acid (78:10:1) as eluent. 5-(4-chlorophenyl)-6-(4-methanesulfonylphenyl)-4-oxo-4H-pyran-2-carboxylic acid (0.13 g) was obtained. m.p. 236° C. (Compound 65 in Table 4).

EXAMPLE 10 a) To a solution of 5-(4-chlorophenyl)-6-(4-methanesulfonylphenyl)-4-oxo-4H-pyran-2-carbaldehyde (0.74 g, 1.9 mmoles) in methylene chloride (10 ml), diethylaminosulfide DAST (0.61 g, 3.8 mmoles) was slowly added at 0° C. The reaction mixture was stirred at this temperature for 1 hour and at room temperature for 16 hours. The mixture was diluted with methylene chloride (10 ml). The organic phase was washed with water, dried ($Na_2SO_4$), and the solvent was removed under reduced pressure. The resulting residue was purified by column chromatography with silica gel and ethyl acetate/n-hexane (1:1) as eluent; 3-(4-chlorophenyl)-6-difluoromethyl-2-(4-methanesulfonylphenyl)pyran-4-one (0.1 g) was obtained. m.p. 168–170° C. (Compound 67 in Table 4).

The 2-phenylpyran-4-one derivatives of general formula (I) included in Table 4 were prepared according to the processes disclosed in these Examples, but with the appropriate starting materials.

TABLE 4

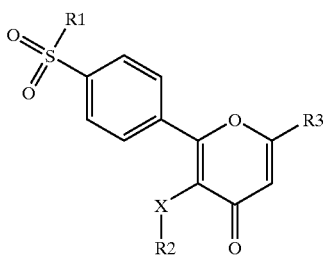

| Compound | R1 | X | R2 | R3 | Method Example | Melting Point (° C.) |
|---|---|---|---|---|---|---|
| 1 | $CH_3$ | single bond | $C_6H_5$ | $CH_3$ | 1 | 185 |
| 2 | $CH_3$ | single bond | 4-$FC_6H_4$ | $CH_3$ | 1 | 237 |
| 3 | $CH_3$ | single bond | 3-$FC_6H_4$ | $CH_3$ | 1 | 182 |
| 4 | $CH_3$ | single bond | 2-$FC_6H_4$ | $CH_3$ | 1 | 136–137 |
| 5 | $CH_3$ | single bond | 4-$ClC_6H_4$ | $CH_3$ | 1 | 182 |
| 6 | $CH_3$ | single bond | 3-$ClC_6H_4$ | $CH_3$ | 1 | 131 |
| 7 | $CH_3$ | single bond | 2-$ClC_6H_4$ | $CH_3$ | 1 | 148 |
| 8 | $CH_3$ | single bond | 4-$BrC_6H_4$ | $CH_3$ | 1 | 198 |
| 9 | $CH_3$ | single bond | 3-$BrC_6H_4$ | $CH_3$ | 1 | 178 |
| 10 | $CH_3$ | single bond | 4-$CH_3C_6H_4$ | $CH_3$ | 1 | 205 |
| 11 | $CH_3$ | single bond | 3-$CH_3C_6H_4$ | $CH_3$ | 1 | 126 |
| 12 | $CH_3$ | single bond | 2-$CH_3C_6H_4$ | $CH_3$ | 1 | 91–93 |
| 13 | $CH_3$ | single bond | 4-$CF_3C_6H_4$ | $CH_3$ | 1 | 172 |
| 14 | $CH_3$ | single bond | 2,3-di$FC_6H_3$ | $CH_3$ | 1 | 187 |
| 15 | $CH_3$ | single bond | 2,4-di$FC_6H_3$ | $CH_3$ | 1 | 208 |
| 16 | $CH_3$ | single bond | 3,4-di$FC_6H_3$ | $CH_3$ | 1 | 207 |
| 17 | $CH_3$ | single bond | 3,5-di$FC_6H_3$ | $CH_3$ | 1 | 210 |
| 18 | $CH_3$ | single bond | 2,5-di$FC_6H_3$ | $CH_3$ | 1 | 183 |
| 19 | $CH_3$ | single bond | 2,6-di$FC_6H_3$ | $CH_3$ | 1 | 206 |
| 20 | $CH_3$ | single bond | 2,3-di$ClC_6H_3$ | $CH_3$ | 1 | 200 |
| 21 | $CH_3$ | single bond | 2,4-di$ClC_6H_3$ | $CH_3$ | 1 | 203 |
| 22 | $CH_3$ | single bond | 3,4-di$ClC_6H_3$ | $CH_3$ | 1 | 156 |
| 23 | $CH_3$ | single bond | 2,5-di$ClC_6H_3$ | $CH_3$ | 1 | 230 |
| 24 | $CH_3$ | single bond | 2,6-di$ClC_6H_3$ | $CH_3$ | 1 | 186 |
| 25 | $CH_3$ | single bond | 6-F, 2-$ClC_6H_3$ | $CH_3$ | 1 | 177 |
| 26 | $CH_3$ | single bond | 2-F, 4-$ClC_6H_3$ | $CH_3$ | 1 | 171 |
| 27 | $CH_3$ | single bond | 4-F, 2-$ClC_6H_3$ | $CH_3$ | 1 | 113 |
| 28 | $CH_3$ | single bond | 4-Cl, 3-$CH_3C_6H_3$ | $CH_3$ | 1 | 98–99 |
| 29 | $CH_3$ | single bond | 3-Cl, 4-$CH_3C_6H_3$ | $CH_3$ | 1 | 176 |
| 30 | $CH_3$ | single bond | 3-F, 4-$CH_3OC_6H_3$ | $CH_3$ | 1 | 137 |
| 31 | $CH_3$ | single bond | 3-Cl, 4-$CH_3OC_6H_3$ | $CH_3$ | 1 | 116 |
| 32 | $CH_3$ | single bond | i-$C_3H_7$ | $CH_3$ | 1 | 108 |
| 33 | $CH_3$ | single bond | $C_6H_{11}$ (cyclohexyl) | $CH_3$ | 1 | 98–99 |
| 34 | $CH_3$ | single bond | 2-naphthyl | $CH_3$ | 1 | 122–123 |
| 35 | $CH_3$ | single bond | 2-indanyl | $CH_3$ | 1 | 169 |
| 36 | $CH_3$ | single bond | 2-tetrahydronaphthyl | $CH_3$ | 1 | 103 |
| 37 | $CH_3$ | $CH_2$ | $C_6H_5$ | $CH_3$ | 1 | 137 |
| 38 | $CH_3$ | O | $C_6H_5$ | $CH_3$ | 2 | 169 |
| 39 | $CH_3$ | O | 4-$FC_6H_4$ | $CH_3$ | 2 | 189 |
| 40 | $CH_3$ | O | 2-$FC_6H_4$ | $CH_3$ | 2 | 178 |
| 41 | $CH_3$ | O | 4-$ClC_6H_4$ | $CH_3$ | 2 | 196 |
| 42 | $CH_3$ | O | 2-$ClC_6H_4$ | $CH_3$ | 2 | 198 |
| 43 | $CH_3$ | O | 4-$BrC_6H_4$ | $CH_3$ | 2 | 188 |
| 44 | $CH_3$ | O | 4-$CH_3C_6H_4$ | $CH_3$ | 2 | 183 |
| 45 | $CH_3$ | O | 2,4-di$FC_6H_3$ | $CH_3$ | 2 | 191 |
| 46 | $CH_3$ | O | 3,4-di$FC_6H_3$ | $CH_3$ | 2 | 194 |
| 47 | $CH_3$ | O | 2,5-di$FC_6H_3$ | $CH_3$ | 2 | 189 |
| 48 | $CH_3$ | O | 2,6-di$FC_6H_3$ | $CH_3$ | 2 | 169 |
| 49 | $CH_3$ | O | 3,4-di$ClC_6H_3$ | $CH_3$ | 2 | 177 |
| 50 | $CH_3$ | O | 2,6-di$ClC_6H_3$ | $CH_3$ | 2 | 170 |
| 51 | $CH_3$ | O | 4-Cl, 3-$CH_3C_6H_3$ | $CH_3$ | 2 | 183 |
| 52 | $CH_3$ | O | 2,3,6-tri$ClC_6H_2$ | $CH_3$ | 2 | 216 |
| 53 | $CH_3$ | O | 2,4,6-tri$ClC_6H_2$ | $CH_3$ | 2 | 171 |
| 54 | $NH_2$ | single bond | $C_6H_5$ | $CH_3$ | 3 | 218 |
| 55 | $NH_2$ | single bond | 4-$FC_6H_4$ | $CH_3$ | 3 | 247 |
| 56 | $NH_2$ | single bond | 3,4-di$ClC_5H_3$ | $CH_3$ | 4 | 128 |
| 57 | $NH_2$ | O | 4-$ClC_6H_4$ | $CH_3$ | 5 | 221 |
| 58 | $CH_3$ | single bond | 4-$ClC_6H_4$ | CN | 6 | 189 |
| 59 | $CH_3$ | single bond | 2,4-di$FC_6H_3$ | CN | 6 | 113 |
| 60 | $CH_3$ | single bond | 4-$ClC_6H_4$ | $CH_2OH$ | 7 | 120 |
| 61 | $CH_3$ | single bond | 4-$BrC_6H_4$ | $CH_2OH$ | 7 | 128–129 |
| 62 | $CH_3$ | single bond | 2,4-di$FC_6H_3$ | $CH_2OH$ | 7 | 173–175 |
| 63 | $CH_3$ | single bond | 4-$ClC_6H_4$ | $CH_2O$-$CH_3$ | 8 | 162 |
| 64 | $CH_3$ | single bond | 2,4-di$FC_6H_3$ | $CH_2O$-$CH_3$ | 8 | 184 |
| 65 | $CH_3$ | single bond | 4-$ClC_6H_4$ | COOH | 9 | 236 |
| 66 | $CH_3$ | single bond | 2,4-di$FC_6H_3$ | COOH | 9 | 241 |
| 67 | $CH_3$ | single bond | 4-$ClC_6H_4$ | $CF_2H$ | 10 | 168–170 |

Examples 11 and 12 illustrate pharmaceutical compositions according to the present invention and procedure for their preparation.

EXAMPLE 11

25,000 capsules each containing 100 mg of 3-(4-chlorophenyl)-2-(4-methanesulfonylphenyl)-6-methylpyran-4-one (active ingredient) were prepared according to the following formulation:

| Active ingredients | 2.5 Kg |
|---|---|
| Lactose monohydrate | 5 Kg |
| Colloidal silicone dioxide | 0.05 Kg |
| Corn starch | 0.5 Kg |
| Magnesium stearate | 0.1 Kg |

Procedure

The above ingredients were sieved through a 60 mesh sieve, and were loaded into a suitable mixer and filled into 25,000 gelatine capsules.

EXAMPLE 12

100,000 Tablets each containing 50 mg of the 3-(2,4-difluorophenyl)-2-(4-methanesulfonylphenyl)-6-methylpyran-4-one (active ingredient) were prepared from the following formulation:

| Active ingredient | 5 Kg |
|---|---|
| Spray dried lactose | 19.9 Kg |
| Microcrystalline cellulose | 3.9 Kg |
| Sodium stearyl fumarate | 0.2 Kg |
| Colloidal silicon dioxide | 0.2 Kg |
| Carboxymethyl starch | 0.8 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

What is claimed is:

1. A compound of formula (I):

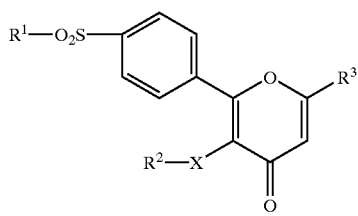

wherein:

$R^1$ represents an alkyl or —$NR^4R^5$ group, wherein $R^4$ and $R^5$ each independently represents a hydrogen atom or an alkyl group;

$R^2$ represents an alkyl, $C_3$–$C_7$ cycloalkyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents a methyl, hydroxymethyl, alkoxymethyl, $C_3$–$C_7$ cycloalkoxymethyl, benzyloxymethyl, hydroxycarbonyl, nitrile, trifluoromethyl or difluoromethyl group or a $CH_2$—$R^6$ group wherein $R^6$ represents an alkyl group; and X represents a single bond, an oxygen atom, a sulfur atom or a methylene group;

or a pharmaceutically acceptable salt thereof.

2. A compound according to claim 1 wherein $R^1$ represents an unsubstituted alkyl group or $NH_2$, $R^2$ represents a branched alkyl, $C_3$–$C_7$ cycloalkyl, naphthyl, tetrahydronaphthyl or indanyl group, an unsubstituted phenyl group or a phenyl group substituted by one or more halogen atoms, alkyl groups and/or alkoxy groups, $R^3$ represents an unsubstituted alkyl group, a nitrile group, a hydroxymethyl group, a methoxymethyl group, a difluoromethyl group or a hydroxycarbonyl group and X represents a single bond, an oxygen atom or a methylene group.

3. A compound according to claim 1 wherein $R^1$ represents a methyl group, $R^2$ represents an unsubstituted phenyl group or a phenyl group substituted by 1, 2 or 3 substituents independently selected from halogen atoms, methoxy groups and methyl groups and $R^3$ represents a methyl group, methoxymethyl group or difluoromethyl group.

4. A compound according to claim 1 wherein $R^2$ represents a phenyl group substituted by 1, 2 or 3 substituents independently selected from halogen atoms methoxy groups and methyl groups, one of the substituents being on the 4-position.

5. A compound according to claim 1 wherein $R^2$ represents a phenyl group substituted by one or two halogen atoms at least one of which is on the 4-position or the 2-position.

6. 3-(4-fluorophenyl)-2-(4-methanesulfonylphenyl)-6-methylpyran-4-one, 3-(2-fluorophenyl)-2-(4-methanesulfonylphenyl)-6-methylpyran-4-one, 3-(4-chlorophenyl)-2-(4-methanesulfonylphenyl)-6-methylpyran-4-one, 3-(4-bromophenyl)-2-(4-methylsulfonylphenyl)-6-methylpyran-4-one, 3-(2,4-difluorophenyl)-2-(4-methanesulfonylphenyl)-6-methylpyran-4-one, 3-(3,4-dichlorophenyl)-2-(4-methanesulfonylphenyl)-6-methylpyran-4-one, 3-(3-chloro-4-methylphenyl)-2-(4-methanesulfonylphenyl)-6-methylpyran-4-one, 2-(4-methanesulfonylphenyl)-6-methyl-3-phenoxypyran-4-one, 3-(4-fluorophenoxy)-2-(4-methanesulfonylphenyl)-6-methylpyran-4-one, 3-(2-fluorophenoxy)-2-(methanesulfonylphenyl)-6-methylpyran-4-one, 3-(4-chlorophenoxy)-2-(methanesulfonylphenyl)-6-methylpyran-4-one, 3-(2-chlorophenoxy)-2-(methanesulfonylphenyl)-6-methylpyran-4-one, 3-(4-bromophenoxy)-2-(4-methanesulfonylphenyl)-6-methylpyran-4-one, 2-(4-methanesulfonylphenyl)-6-methyl-3-(4-methylphenoxy)pyran-4-one, 3-(2,4-difluorophenoxy)-2-(4-methanesulfonylphenyl)-6-methylpyran-4-one, 3-(2,5-difluorophenoxy)-2-(methanesulfonylphenyl)-6-methylpyran-4-one, 3-(4-chlorophenyl)-2-(4-methanesulfonylphenyl)-6-methoxymethylpyran-4-one, 3-(4-chlorophenyl)-6-difluoromethyl-2-(4-methanesulfonylphenyl)pyran-4-one, and pharmaceutically acceptable salts thereof.

7. A process for the preparation of a compound of claim 1 which process comprises:

(a) wherein $R^1$ is an alkyl or —$NR^4R^5$ group in which $R^4$ and $R^5$ each independently is an alkyl group, $R^3$ is a methyl group, reacting a carbonyl derivative of formula (III)

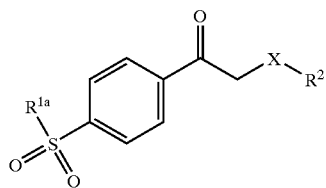

(III)

wherein $R^{1a}$ is an alkyl or a —$NR^{4a}R^{5a}$ group in which $R^{4a}$ and $R^{5a}$ are each independently alkyl groups with an excess of anhydrous acetic acid and polyphosphoric acid at a temperature from 100° C. to 150° C.;

(b) wherein $R^1$ is an alkyl group, $R^3$ is a methyl group, with the proviso that X is other than a sulfur atom, reacting a mercapto derivative of formula (VIII):

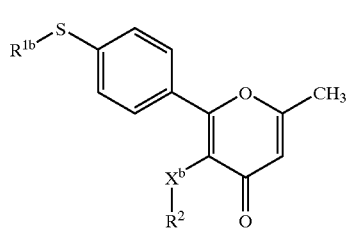

(VIII)

wherein $R^{1b}$ is an alkyl group, $X^b$ is X with the proviso that it is other than a sulfur atom with an oxidizing agent;

(c) wherein $R^1$ is a —$NR^4R^5$ group, $R^3$ is a methyl group reacting a chlorosulfonyl derivative of formula (X):

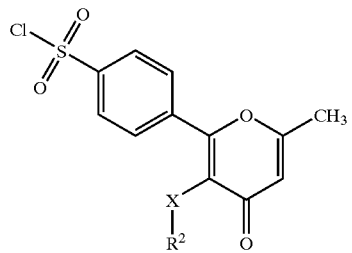

(X)

with an amine of formula (XI):

$R^4$—NH—$R^5$ (XI)

or (d) wherein $R^1$ is a —$NR^4R^5$ group wherein $R^4$ and $R^5$ are hydrogen, $R^3$ is a methyl group, by debenzylation of the corresponding N,N-dibenzyl derivative of formula (XIV)

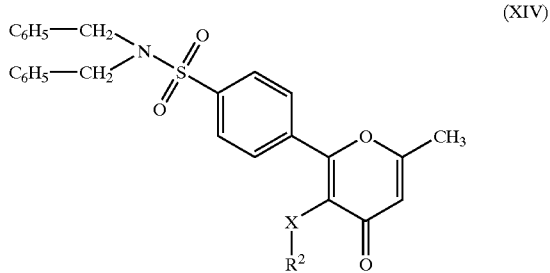

(XIV)

8. A composition comprising a compound according to any one of claims 1 to 6 or pharmaceutically acceptable salt thereof in admixture with a carrier or diluent.

9. A method of treating pain, fever or inflammation or inhibiting prostanoid-induced smooth muscle contraction which comprises administering to an animal subject in need of treatment an effective amount of a compound of any one of claims 1 to 6.

10. The method according to claim 9 wherein the compound is administered to a human subject in need of treatment.

* * * * *

UNITED STATES PATENT AND TRADEMARK OFFICE
CERTIFICATE OF CORRECTION

PATENT NO. : 6,518,303 B2
DATED : February 11, 2003
INVENTOR(S) : Crespo Crespo et al.

It is certified that error appears in the above-identified patent and that said Letters Patent is hereby corrected as shown below:

<u>Title page,</u>
Insert the following item:
-- [30]  Foreign Application Priority Data
September 25, 1998 [ES]  Spain..........P9802011
March 26, 1999   [ES]    Spain..........P9900619 --

Signed and Sealed this

Ninth Day of March, 2004

JON W. DUDAS
*Acting Director of the United States Patent and Trademark Office*